(12) United States Patent
Pepin (10) Patent No.: US 11,152,094 B2
(45) Date of Patent: Oct. 19, 2021

(54) SYSTEMS AND METHODS FOR A CONNECTED MEDICATION DISPENSER

(71) Applicant: Verily Life Sciences LLC, South San Francisco, CA (US)

(72) Inventor: Brian Pepin, San Francisco, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 87 days.

(21) Appl. No.: 16/327,676

(22) PCT Filed: Sep. 26, 2017

(86) PCT No.: PCT/US2017/053498
§ 371 (c)(1),
(2) Date: Feb. 22, 2019

(87) PCT Pub. No.: WO2018/067349
PCT Pub. Date: Apr. 12, 2018

(65) Prior Publication Data
US 2019/0198147 A1 Jun. 27, 2019

Related U.S. Application Data

(60) Provisional application No. 62/403,317, filed on Oct. 3, 2016.

(51) Int. Cl.
*A61J 7/00* (2006.01)
*G16H 20/13* (2018.01)
(Continued)

(52) U.S. Cl.
CPC ............... *G16H 20/13* (2018.01); *A61J 7/00* (2013.01); *A61J 7/04* (2013.01); *G16H 40/63* (2018.01);
(Continued)

(58) Field of Classification Search
None
See application file for complete search history.

(56) References Cited

U.S. PATENT DOCUMENTS 8,581,709 B2 * 11/2013 Mazur .................... G16H 20/13
340/309.16
2013/0195326 A1  8/2013 Bear et al.
(Continued)

FOREIGN PATENT DOCUMENTS

WO  2014198648 A1  12/2014
WO  2016138047 A1  9/2016

OTHER PUBLICATIONS

International Search Report and Written Opinion from the International Searching Authority dated Jan. 3, 2018, for International Application No. PCT/US2017/053498, filed Sep. 26, 2017, 16 pages.

*Primary Examiner* — Gene O Crawford
*Assistant Examiner* — Ayodeji T Ojofeitimi
(74) *Attorney, Agent, or Firm* — Christensen O'Connor Johnson Kindness PLLC (57) ABSTRACT

The present disclosure relates to systems, methods, and computer-readable storage devices medication adherence systems. A container may be provided with a computing unit and display screen. The display screen may be integrated into an interior surface of the container or each compartment within the container. The display screen may display messages to a user about loading the container, the contents of the container, and/or removing contents from the container. A second display screen may also be provided on a lid of the container.

27 Claims, 10 Drawing Sheets

(51) Int. Cl.
*G16H 40/63* (2018.01)
*A61J 7/04* (2006.01)
(52) U.S. Cl.
CPC ........ *A61J 2200/30* (2013.01); *A61J 2200/74* (2013.01)

(56) References Cited

U.S. PATENT DOCUMENTS

| | | |
|---|---|---|
| 2014/0261883 A1 | 9/2014 | Dent et al. |
| 2016/0022541 A1* | 1/2016 | Dalal .................... G06Q 50/22 221/9 |
| 2018/0344575 A1* | 12/2018 | Brady .................. A61J 7/0084 |

* cited by examiner

SYSTEMS AND METHODS FOR A CONNECTED MEDICATION DISPENSER

CROSS-REFERENCE TO RELATED APPLICATIONS

This application claims the benefit of U.S. Provisional Application No. 62/403,317, filed Oct. 3, 2016, which is incorporated by reference in its entirety.

TECHNICAL FIELD

This disclosure relates generally to medication adherence systems. More specifically, this disclosure relates to systems, devices, and methods for a connected medication container with visual indications for medication compliance.

BACKGROUND

Patient compliance with medication dosing schedules is a serious problem. A majority of prescribed medication is not taken as directed. Non-compliance leads to worsening illness, hospitalization, irreversible loss of function, and death, resulting in tremendous human and financial costs. When medicines are taken, especially outside hospitals, errors in selection of the correct pill and the appropriate dose add further morbidity and mortality.

Managing the medication taking process can be frustrating and confusing. Doctors prescribe multiple medications for different health conditions. Some medications might be taken daily, others twice a day, and yet others 3-4 times a day. When multiple medications are prescribed and each is to be taken at different intervals, it can become difficult to remember when each medication is to be taken, and thus there is a need for a simple management system for such pill-taking. For example, elderly patients and patients taking multiple medications at different dosing schedules may have difficulty remembering to take their medications at the scheduled times.

Furthermore, correctly loading multi-day medication dispensers is error prone. Multi-day medication dispensers require a patient to load different compartments with different mixtures of pills. Different medication often looks similar and obtaining the proper mix per day can be confusing. Furthermore, once a multi-day medication dispenser is loaded, it can be cumbersome and difficult to alter a medication regimen. In this situation, a patient would be required to unload the dispenser, sort the pills, and then reload the dispenser.

Other medications, such as opioid analgesics and narcotics, may be prone to abuse or diversion, for instance taken in excess or diverted and sold to others who would abuse the medication. Groups of people in which non-compliance is a common problem include Americans with chronic disease, diabetes (approximately 18 million), cardiovascular diseases (approximately 58 million), depression (approximately 20 million), and asthma (approximately 17 million).

It would be desirable to enhance patient adherence to dosing schedules for prescription medications. It would be useful to provide a low-cost dispenser and monitoring system that can assist a patient properly loading the dispenser and informing the patient when to take medication and how much to take. It also would be useful to provide a dispenser and monitoring system to verify that medication stored therein are removed by the patient to prevent diversion. It would also be useful to provide a dispenser and monitoring system to allow a patient to change a prescription plan without having to reload the dispenser.

SUMMARY

Certain embodiments of the present disclosure relate to a container for dispensing medication. The container may include one or more storage compartments, a computing unit, and one or more display screens. The one or more compartments may be dimensioned to store medication, and the computing unit may be configured to process information about the contents of the one or more storage compartments. The one or more display screens may be disposed on a floor of the container and coupled to the computing unit. The one or more display screens may also be configured to display the processed information about the contents of one or more storage compartments. Certain embodiments of the present disclosure relate to a method of tracking medication usage. The method may include providing a display screen on a floor of a storage compartment of a container. The display screen may be visible when the container is open. The method may further include displaying, by the display screen, an indication to add medication to the storage compartment and determining an amount of medication in the storage compartment. The method may also include comparing the amount of medication in the storage compartment with a predetermined amount of medication and displaying a message based on the comparison of the amount of medication in the storage compartment with a predetermined amount of medication on the display screen.

Certain embodiments of the present disclosure relate to a method of tracking medication usage. The method may include providing a medication container comprising a computing unit and a display unit that may be disposed on the bottom surface of the container. The method may further include receiving a prescription plan by the computing unit and displaying, by the display screen, an amount of medication required in the container.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the disclosed principles. In the drawings.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems and methods described herein should not be construed as limiting in any way. Instead, the present disclosure is directed toward all novel and non-obvious features and aspects of the various disclosed embodiments, alone and in various combinations and sub-combinations with one another. The disclosed systems and methods are not limited to any specific aspect or feature or combinations thereof, nor do the disclosed systems and methods require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Systems and methods consistent with the present disclosure are directed to a connected container with at least one storage compartment. In some embodiments, the storage compartment may store medication, such as pills. The storage compartment may have a display screen on its bottom surface and have a computing unit coupled to the display screen. In some embodiments, the display screen may direct a user, such as a patient, to fill the one or more compartments with items, such as medication. In other embodiments, the display screen may direct a user to take specific items out of the one or more storage compartments.

In some embodiments, the container may have more than one compartment and one or more display screens at the bottom of each compartment. The display screens may display different information to a user at the same time. In some embodiments, the computing unit may receive information from a remote device, which information may be displayed on the one or more display screens.

A user may be a patient or other person that takes medication, health supplements, vitamins, or other pills.

Figure 1:
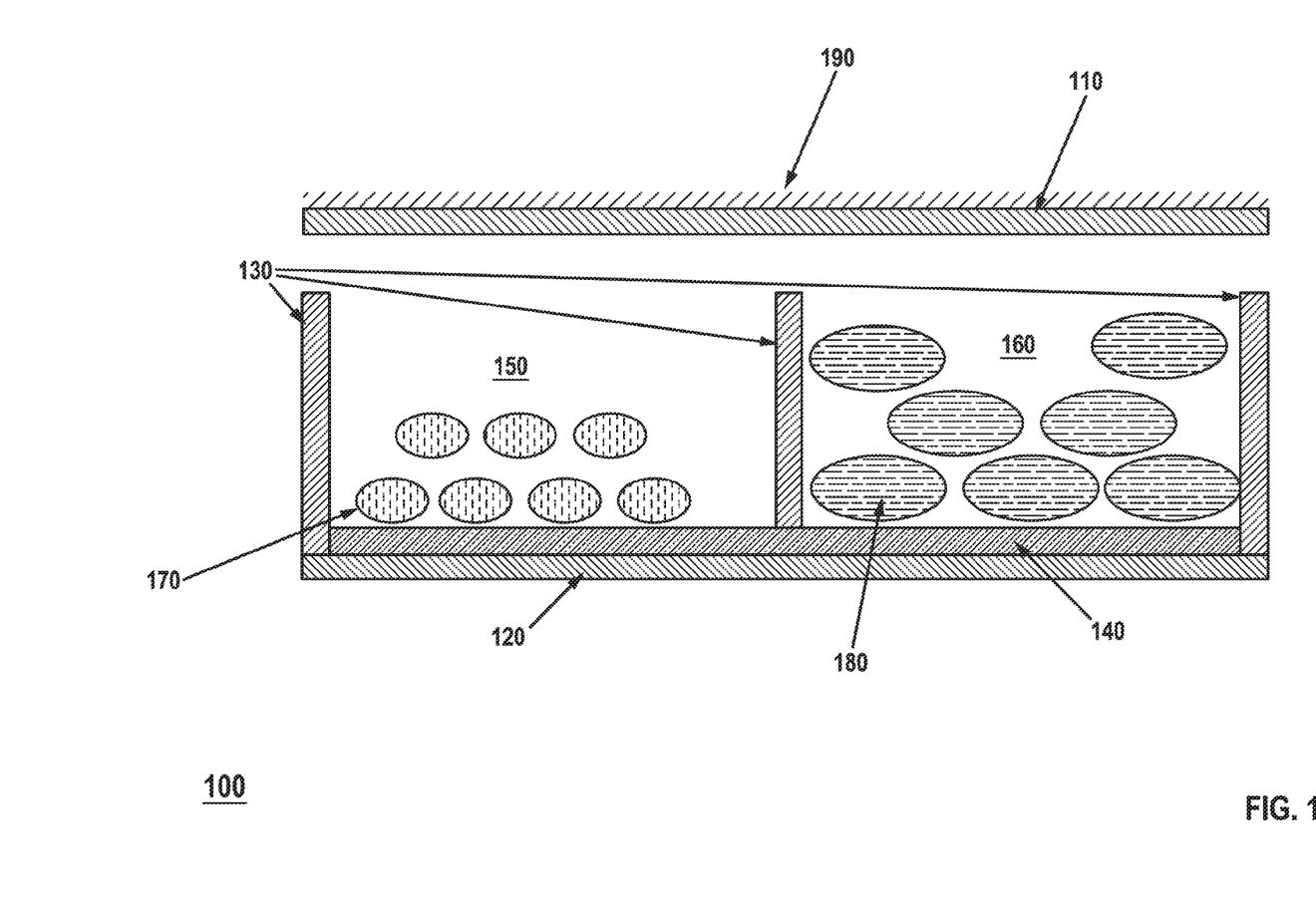
FIG. 1 illustrates an exemplary container, consistent with embodiments of the present disclosure.

FIG. 1 illustrates and exemplary container 100 that may be used to store medication or other pill sized items. As shown in FIG. 1, container 100 may comprise a lid 110, a floor 120, and sidewalls 130. Container 100 may also have a display screen 140 on the floor of the container 100. In some embodiments, container 100 may also have a second display screen 190 on the lid 110. Display screen 140 and/or 190 can also comprise separate display screens in each or some of the compartments or lids, as described herein.

In some embodiments, container 100 may have an overall dimension small enough to fit in a user's pants pocket or purse. For example, container 100 may be approximately three inches by three inches by one inch thick. While these dimensions are just an example, the container 100 is small enough to fit in a user's hand.

In some embodiments, container 100 may have two or more storage compartments 150 and 160. In other embodiments, container 100 may only have one storage compartment. While only two storage compartments 150 and 160 are show, container 100 may have any number of compartments. Storage compartments, 150 and 160 may be separated by sidewalls 130, forming the compartments. The compartments may be sized to store medication or other pill-sized items.

In some embodiments, display screen 140 may be attached to an interior surface of the container. In some embodiments, display screen 140 may be a single screen on the floor 120 of container 100. Sidewalls 130 may be affixed to the screen to form compartments 150 and 160. In other embodiments, display screen 140 may be comprised of a plurality of separate screens, each affixed to the floor 120 of a compartment. Display screen 140 may be integrated into the floor 120 or affixed to it. In still other embodiments, display screen 140 may be attached to sidewalls 130, so that it can be seen if items are placed in the compartments and obscure the floor. In some examples, display screen 140 may be an LCD display, an OLED display, E ink, etc. In some embodiments, the display screen 140 may be a touch screen. The display screen 140 may be glued or screwed onto the floor 120 to provide a tight fit.

In some embodiments, display screen 140 may be coupled to a computing unit (not shown). The computing unit maybe attached to, or integrated into the floor 120. In other embodiments, the computing unit may be attached to, or integrated into one or more sidewalls 130. A battery (not shown) may also be integrated into floor 120 or sidewalls 130. The battery may supply power to the computing unit and to the display screen. In some embodiments, the computing unit may be configured to receive information wirelessly (e.g., through WiFi, Bluetooth®, Bluetooth® LE, ZigBee®, etc.). In other embodiments, the computing unit may be configured to receive information through a wired connection (e.g., USB, Firewire, Lightning, etc.). The computing unit may be configured to process the received information and cause the display screen 140 to display information to the user (e.g., instructions, status of the container, etc.), as described below.

In some embodiments, display screen 140 may include a force sensor (not shown) or some other sensor to measure the contents of compartments 150 and 160. The sensor may be connected to the computing unit and configured to send data to the computing unit for further processing. In the case of a force sensor, the weight of items in a compartment may be measured to determine how many items are in that compartment.

In some embodiments, compartments 150 and 160 may be used to store pills, such as medication 170 and 180. The pills may rest atop display screen 140. Lid 110 may cover compartments 150 and 160 to prevent the pills from falling out of container 100.

In some embodiments, a second display screen 190 may be attached to lid 110. In some examples, the second display screen 190 may be attached the exterior surface of the lid 110. In other examples, the second display screen may be attached to the inner surface of the lid 110. Second display screen 190 may receive information to display from the computing unit. Power may be supplied to the second display screen 190 through connectors in the sidewalls 130. Alternatively, power may be supplied by a battery in the lid 110. In some examples, display screen 190 may be an LCD display, an OLED display, E ink, etc. In other examples, display screen 190 may be electrochromic glass that can be configured to change from transparent to clear.

In some embodiments, a camera may be attached to lid 110. The camera may be configured to image the contents of container 100. For example, the camera may take pictures of the contents of each compartment 150 and 160. The pictures may be sent to the computing unit for further processing. In some embodiments, the computing unit may process the pictures to determine the amount and type of contents of each compartment. In some examples, the computing unit may determine the number of pills in a compartment and the type of medication that the pills are.

Figure 2:
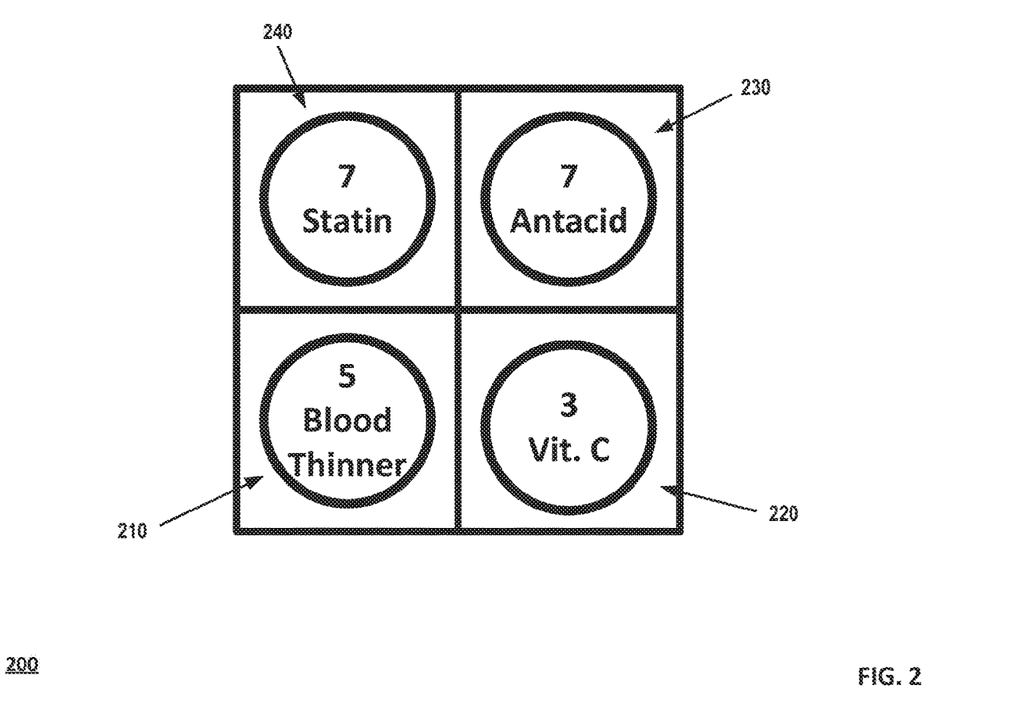
FIG. 2 illustrates an example container system with indicators to load medication, consistent with embodiments of the present disclosure.

FIG. 2 illustrates an example container system 200 with indicators to load medication. As shown in FIG. 2, container system 200 comprises a container with four compartments 210, 220, 230, and 240, where each compartment may be as described with regard to FIG. 1. Each compartment 210, 220, 230, and 240 may have a display screen on the floor of the compartment, as described above.

As shown in FIG. 2, the display screen on the floor of each compartment 210, 220, 230, and 240 may display information to a user indicating how many of a certain type of medication is required to be deposited in each compartment. For example, compartment 210 may display a message that "5 Blood Thinner" are to be deposited in it (e.g., Plavix®); compartment 220 may display that "3 Vit. C" are to be deposited in it; compartment 230 may display that "7 Antacid" are to be deposited in it (e.g., Nexium®); and compartment 240 may display that "7 Statin" are to be deposited in it (e.g., Pravastatin®). In some embodiments, the color of the displayed message may be changed to indicate whether more pills should be added, too many pills are present, or the compartment is full (e.g., correct number of pills are present). For example, the message may be displayed in blue when more pills are required, in red when too many pills are present, and the message may be removed when the correct number of pills are in the compartment.

Figure 3:
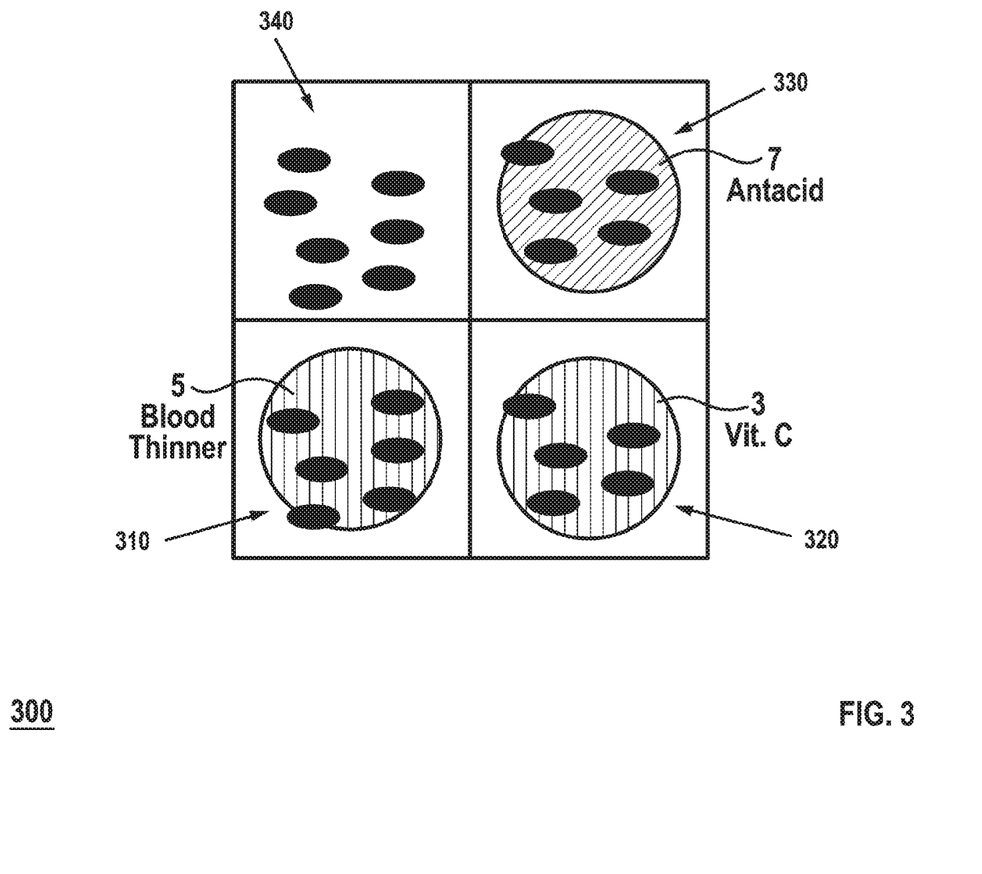
FIG. 3 illustrates an example container system with indicators of proper or improper loading, consistent with embodiments of the present disclosure.

FIG. 3 illustrates an example container system 300 with indicators of correct and incorrect loading. As shown in FIG. 3, container system 300 comprises a container with four compartments 310, 320, 330, and 340, where each compartment may be as described with regard to FIG. 1. Each compartment 310, 320, 330, and 340 may have a display screen on the floor of the compartment, as described above.

As shown in FIG. 3, the display screen on the floor of each compartment 310, 320, 330, and 340 may display information to a user indicating whether the correct amount of medication is in a respective compartment. For example, a user may have been instructed to deposit a predetermined number of pills in each compartment, as described above. After depositing pills in the container system 300, compartment 310 may contain 6 pills, compartments 320 and 330 may each contain 5 pills, and compartment 340 may contain 7 pills. Container system 300 may determine the number of pills in each compartment, as described herein, and indicate to the user whether the correct number of pills are in each compartment.

In the example shown in FIG. 3, compartment 310 required "5 Blood Thinner" and 6 pills are present. When too many pills are present in the compartment, the display screen may display a visual indication that pills should be removed. For example, the message "5 Blood Thinner" may be changed to red (as indicated by vertical lines in the figure) to indicate that too many pills are in compartment 310. Similarly, compartment 320 may contain 5 pills, when 3 pills are indicated on the display screen. In this case, "3 Vit. C" may also be displayed in red. The example further shows that compartment 330 may contain 5 pills but the display screen indicated that the compartment 330 should contain 7 pills. In this case the message may be displayed in blue (as indicated by diagonal lines in the figure) to indicate too few pills are in the compartment 330. As further shown in the example, compartment 340 may contain 7 pills. In this case the message "7 Statin" may be removed because the correct number of pills are present in the compartment 340.

It should be noted that any particular colors described above are only examples and other colors may be chosen. Further, different patterns, flashing messages, changed text, etc., may be used to indicate user actions regarding the contents of a compartment.

Figure 4:
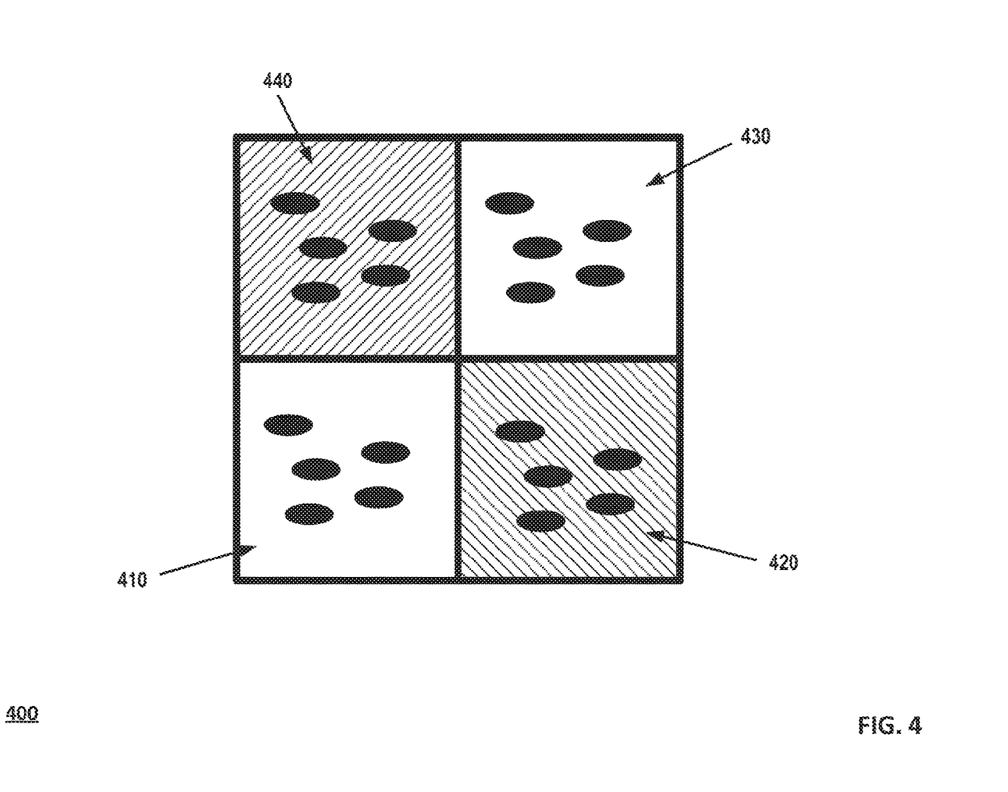
FIG. 4 illustrates an example container system with indicators to take medication, consistent with embodiments of the present disclosure.

FIG. 4 illustrates an example container system 400 with indicators to take medication. As shown in FIG. 4, container system 400 comprises a container with four compartments 410, 420, 430, and 440, where each compartment may be as described with regard to FIG. 1. Each compartment may contain a number of pills resting on top of a display screen. In some embodiments, the computing unit may determine that a user should take certain medication from one or more of the compartments. The computing unit may receive the information from a remote device, or the computing unit may use an algorithm to determine when medication should be taken. The algorithm may be based on a prescription plan downloaded into the computing unit.

When the computing unit determines that it is time for the user to take medication, the computing unit may cause the display screen to indicate from which compartment pills should be taken. As shown in FIG. 4, the display screen on the floor of compartments 420 and 440 are lit up to indicate that the medication in those compartments should be taken. The display screen may display a color or pattern to indicate how many pills to take and/or whether too many pills have been taken.

Figure 5:
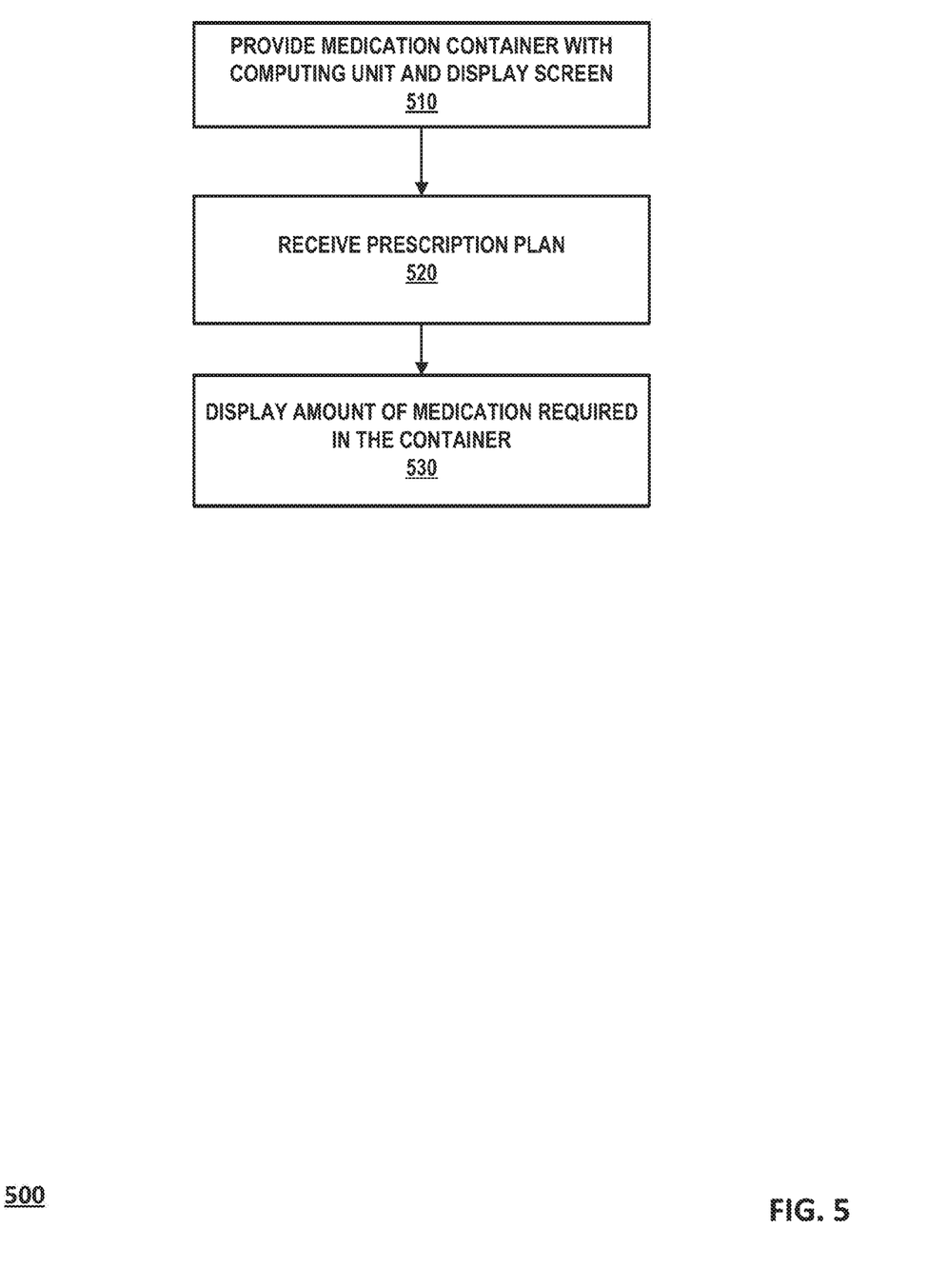
FIG. 5 is a flowchart illustrating an exemplary method of loading a container, consistent with embodiments of the present disclosure.
Figure 10:
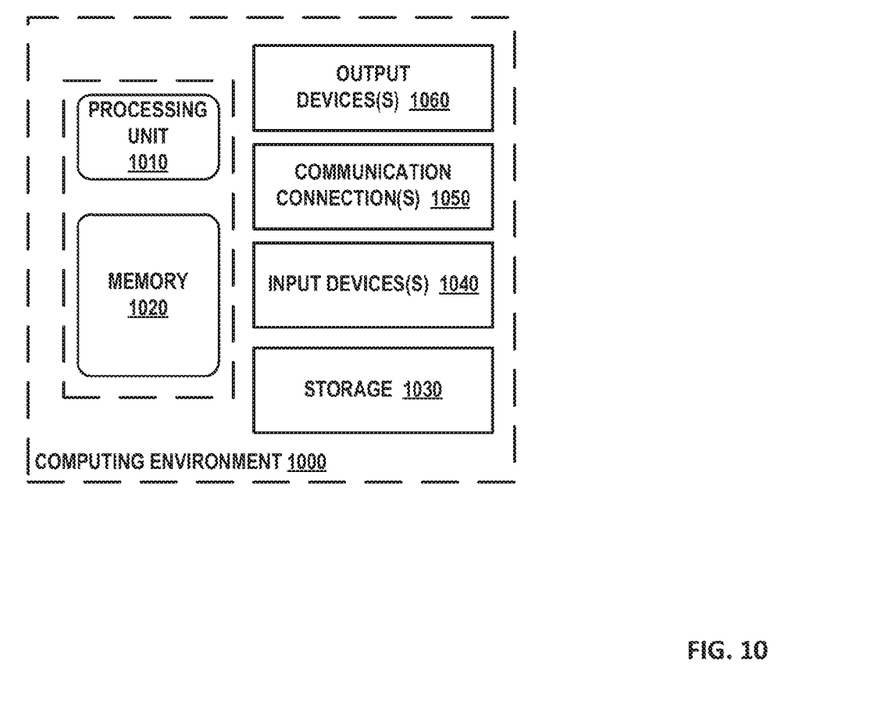
FIG. 10 illustrates an exemplary computing environment, consistent with embodiments of the present disclosure.

FIG. 5 is a flowchart of an exemplary method 500 of loading a container system and can be implemented for example in a system shown in FIG. 1. It should be noted that the methods described herein are consistent with different operating systems or hardware and can be applied in any variety of environments to take advantage of the described features. For example, computing environment 1000 may be used to perform the described steps.

At step 510, a medication container with a computing unit and display screen is provided. The medication container may be as described in FIG. 1.

At step 520, the medication container may receive a prescription plan. The computing unit in the container may receive the prescription plan either wirelessly or through a wired connection. In some examples, the prescription plan may be received from cloud computing resources and transmitted to the container from a networked device, such as phone, PDA, personal computer, etc. In some embodiments, the prescription plan may be data that indicates which medication should be taken by a patient and at what times the medication should be taken. The prescription plan may also comprise data about the size and color of pills for certain medications.

In some embodiments, a new prescription plan may be received with updated information to alter an existing prescription plan. For example, a physician may update an existing prescription plan and send it to the container (e.g., directly or indirectly), whereby the container may process the new prescription to indicate a different combination of medication to be taken. Because the container "knows" the type and quantity of pills that are loaded into compartments in the container, mixtures of pills may be updated at any time. This allows medication regimens to be altered without causing the user to manually determine a mixture of medication, which is prone to error.

At step 530, the display screen may display an amount of medication to be placed in each compartment. In some embodiments, the computing unit may process the prescription plan to determine the number of pills in each compartment. In some examples, the computing unit may cause the display screen to display one or more messages related to the prescription plan, such as loading instructions. In some examples, the computing unit may determine which compartment is best suited for a particular medication in the prescription plan.

In some embodiments, the computing unit may comprise communication connections, such as an on-board radio, and communicate with a remote device and/or cloud computing resources. In some examples, the container may sense data about its contents (e.g., weight, images, open/closed, etc.) and transmit the data to the remote device or cloud. The data may be analyzed and combined with the prescription plan and new data transmitted back to the computing unit, which may analyze the data and display the information on the display screen. Because the current state of the container and the prescription plan are known, the display screen shows the most current information to the user. In other examples, the prescription plan may be stored in the computing unit. In this case, the container may process the information to display the most current information.

Figure 6:
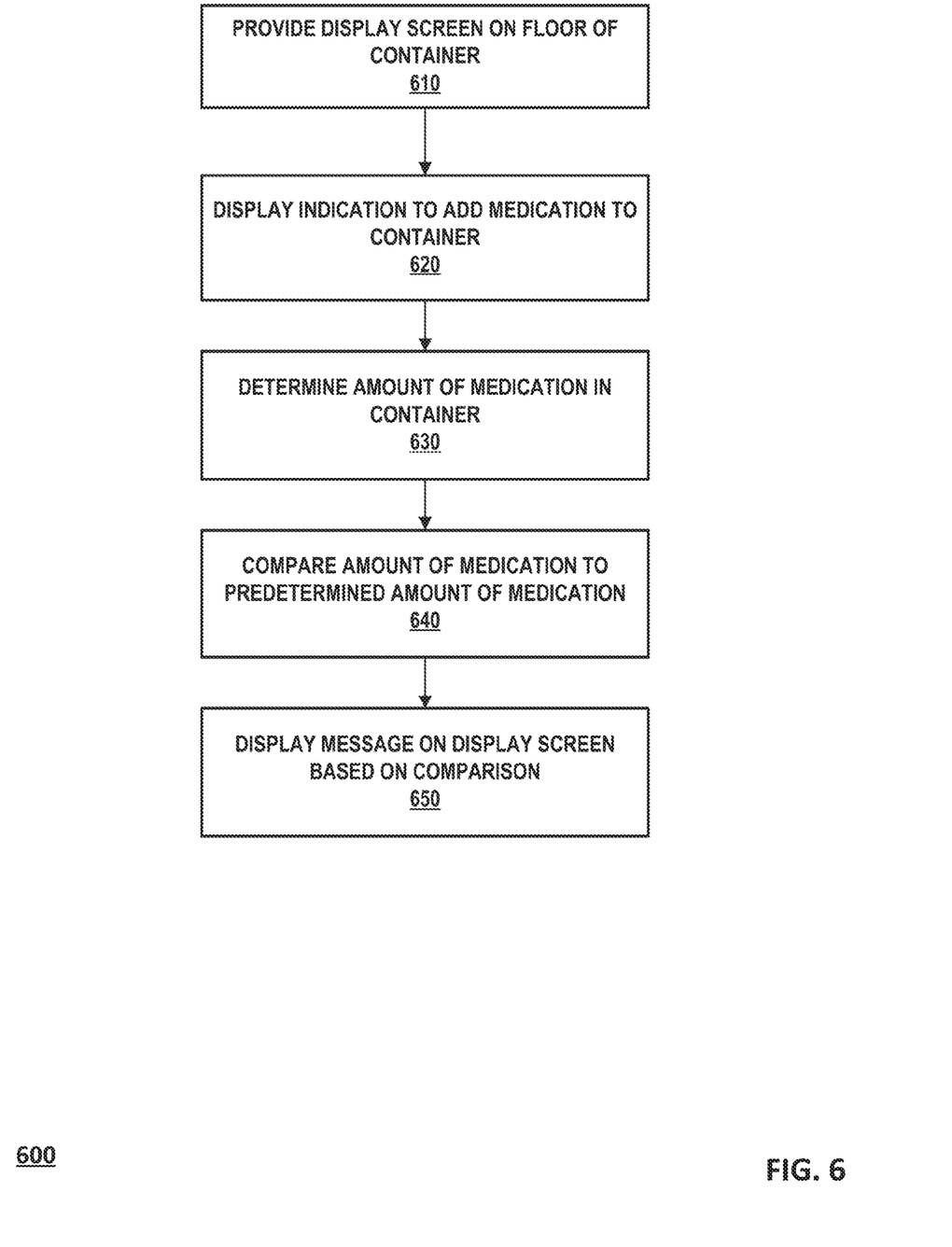
FIG. 6 is a flowchart illustrating an exemplary method of indicating that a container is loaded correctly, consistent with embodiments of the present disclosure.

FIG. 6 is a flowchart of an exemplary method 600 of indicating that a container is loaded correctly and can be implemented for example in a system shown in FIG. 1.

At step 610 a medication container with a computing unit and display screen is provided. The medication container may be as described in FIG. 1.

At step 620, an indication (e.g., message) to add medication to the container may be displayed on the display screen. In some embodiments, the computing may process a prescription plan and determine the type and quantity of medication to be place in the container. In some examples, the container may comprise a plurality of compartments and the display screen may be segmented to display separate messages in each compartment.

At step 630, the amount of medication in the container is determined. In some embodiments, a force sensor may be integrated into the display screen, or alternatively the floor of the container. The force sensor may transmit to the computing unit a signal representative of the weight of the contents of the container. The computing unit may determine the amount of medication based on the sensed weight and data contained in the prescription plan (e.g., weight of individual pills).

In some embodiments, a camera may be attached or integrated into the lid of the container and configured to take pictures of the contents of the container. The pictures may be transmitted to the computing unit. The computing unit may determine the amount of medication based on the pictures and data contained in the prescription plan (e.g., size of individual pills). For example, the computing unit may use machine vision algorithms to determine the number of individual pills.

At step 640, the determined amount of medication may be compared to a predetermined amount of medication. In some embodiments, the predetermined amount of medication may be determined from the prescription plan. In some embodiments, the computing unit may determine the amount of medication in the container and compare that amount to the predetermined amount periodically. For example, while the user is loading the container, the computing unit may compare the determined amount of medication to the predetermined amount of medication once every second. In some examples the computing may compare every 0.1 s, 0.5 s, 1 s, 5 s, etc.

At step 650, a message, which content is based on the comparison, may be displayed on the display screen. In some embodiments, the display screen may be updated periodically based on the comparison. The message on the display screen may indicate that too few pills, too many pills, or a correct number of pills are present in the container.

Figure 7:
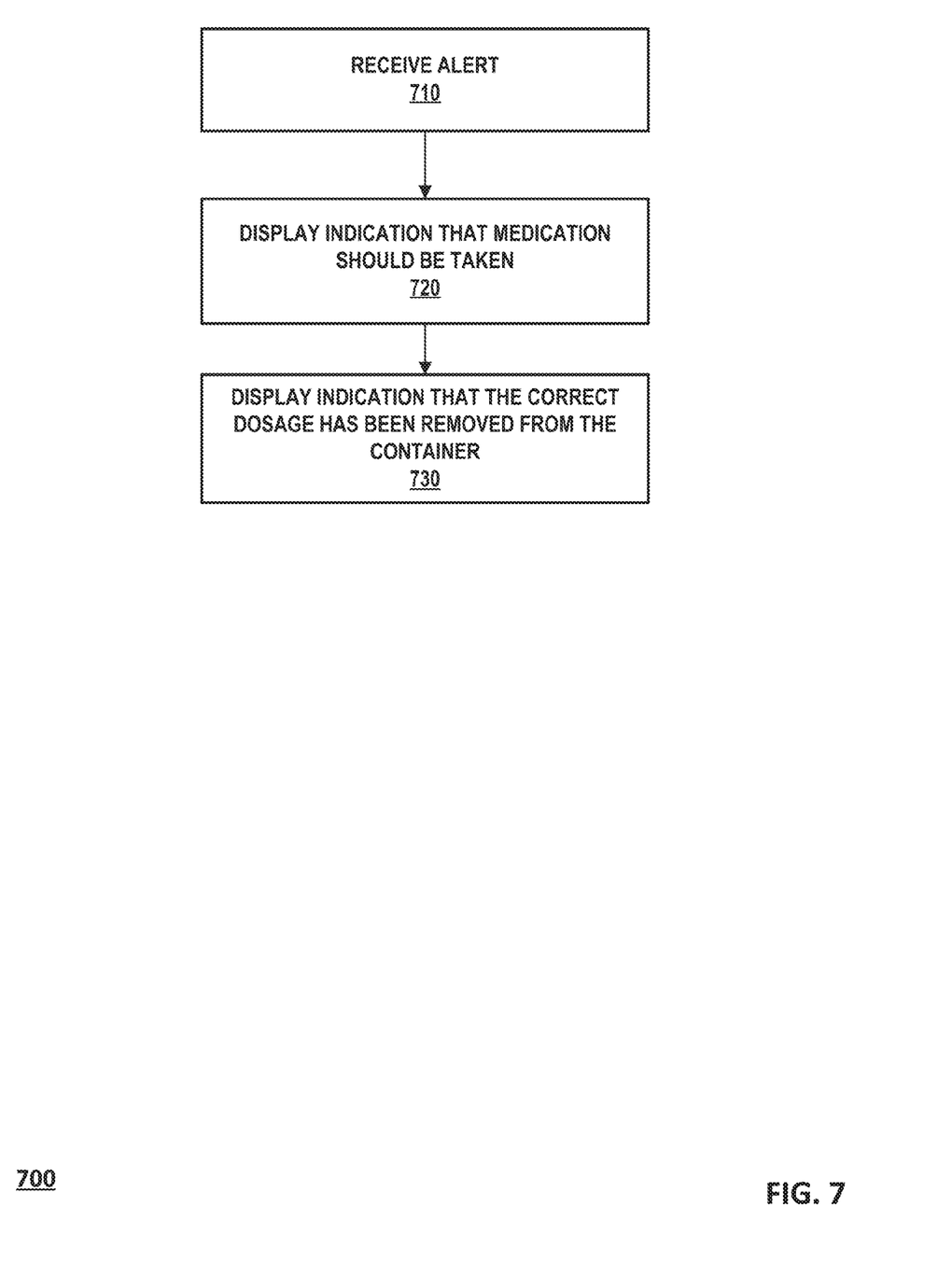
FIG. 7 illustrates is a flowchart illustrating an exemplary method of indicating dosage to a user, consistent with embodiments of the present disclosure.

FIG. 7 is a flowchart of an exemplary method 700 of indicating dosage to a user and can be implemented for example in a system shown in FIG. 1.

At step 710, an alert is received. In some embodiments, the alert may be received by the computing unit in the container. In some embodiments, the alert may be received by a remote computing device and transmitted to the computing unit in the container. In some examples, the alert may be an indication that the user take medication at a predetermined time. The alert may also indicate which medication the user is to take.

At step 720, an indication may be displayed that medication should be taken. For example, the computing unit may cause the display screen to display a message, as described above, indicating that medication in a particular compartment be removed. In this way, dosages for specific days need not be prearranged. For example, a prescription plan may call for a certain combination of pills on Monday and different combination of pills on Tuesday. By indicating which pills are to be taken and the time they are to be taken, the pills need not be presorted. Thus, each type of pill can occupy its own compartment, and the user can remove the indicated number of pills from the indicated comparts at the indicted time.

In some embodiments, a prescription plan may be received with updated information to alter an existing prescription plan. For example, a physician may update a prescription plan and send it to the container (e.g., directly or indirectly), whereby the container may process the new prescription to indicate a different combination of medication to be taken. Because the container "knows" the type and quantity of pills that are loaded into compartments in the container, mixtures of pills may be updated at any time.

At step 730, an indication that the correct dosage has been removed from the container may be displayed. For example, the display screen may flash a color under the pills to be taken, and when the user removes a predetermined number of pills, the display screen may stop flashing. In some embodiments, the predetermined number of pills may be determined from the prescription plan, as described above.

Figure 8:
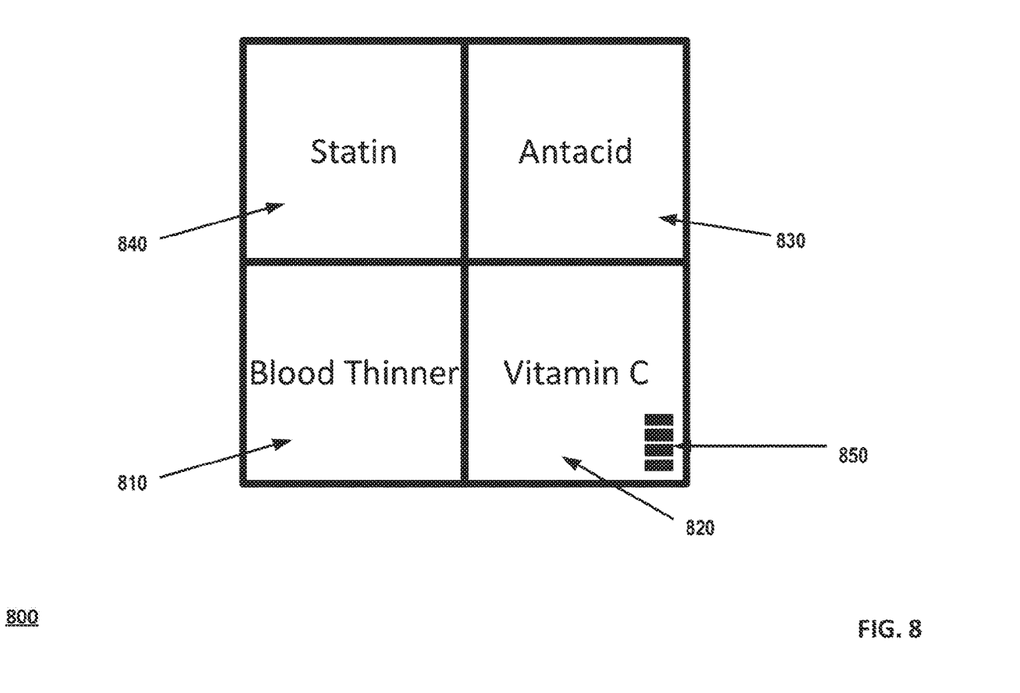
FIG. 8 illustrates an example container display showing contents of the dispenser, consistent with embodiments of the present disclosure

FIG. 8 illustrates an example container display 800 showing contents of the container. The container display 800 may comprise an LCD, OLED, E ink, or similar screen. In some embodiments, container screen 800 may be affixed to the lid of a container, such that it can be seen when the container is closed. In some embodiments, the container display 800 be transparent when off, such that the contents of the container may be seen, and opaque when on (e.g., electrochromic glass).

In some embodiments, container display 800 may receive information from the computing unit in the container. In other embodiments, a second computing unit may be connected to the container display 800. Container display 800 may use the same or a different power source as the computing unit and the display screen on the floor of the container.

In some embodiments, container display 800 may display a summary of the contents of the container. As shown in FIG. 8, container display 800 may be segmented into a plurality of segments corresponding to compartments in the container. For example, segments 810, 820, 830, and 840 may correspond to four compartments in the container (e.g., as shown in FIGS. 2, 3, and 4). In some embodiments, container display 800 may display the contents of the container. For example, segment 810 may display "Blood Thinner," segment 820 may display "Vitamin C," segment 830 may display "Antacid," and segment 840 may display "Statin." Other messages may be displayed depending on the contents of the container. For example, the amount of items in a compartment may be displayed. In other examples, a picture of the contents of the container or compartment may be displayed.

In some embodiments, a power indicator 850 may be displayed. Power indicator 850 may show the amount of battery life left for the container.

Figure 9:
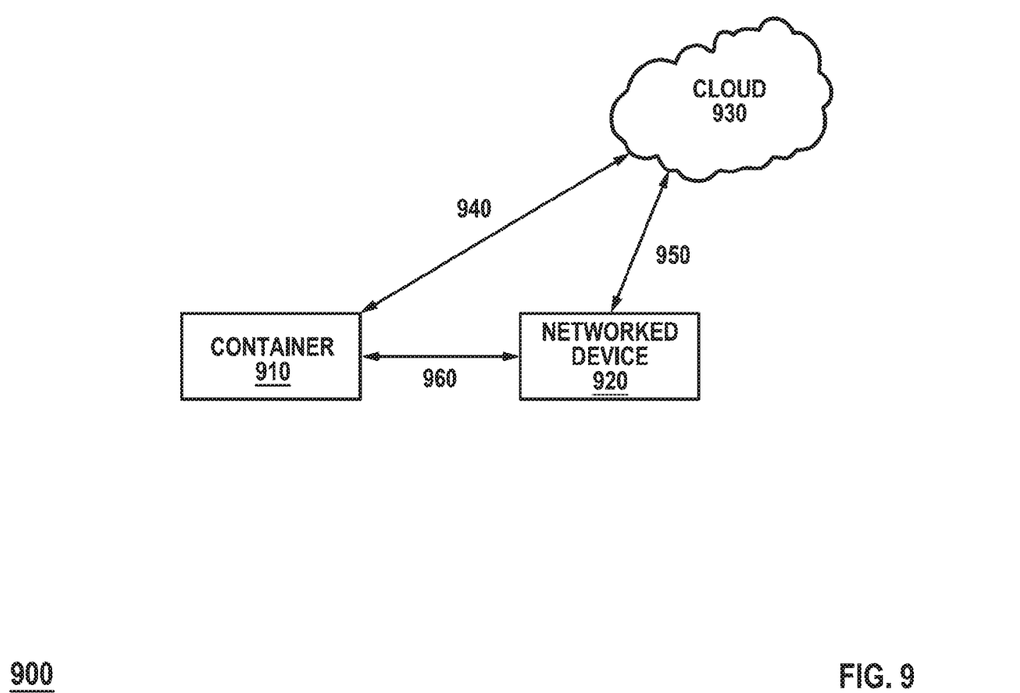
FIG. 9 illustrates an example container system, consistent with embodiments of the present disclosure.

FIG. 9 illustrates an example container system 900 comprising a container 910, a networked device 920 and cloud computing resources 930. Container 910 may be similar to the container described in FIG. 1.

In some embodiments, container 910 may communicate directly with cloud computing resources 930 though communication link 940. Communication link 940 may be through WiFi, cellular link, or the like. Container 910 may use the link to receive a prescription plan stored in cloud computing resources 930. In some embodiments, cloud computing resources 930 may receive and store prescription information (e.g., prescription plan), electronic medical records for the user, container content information, etc. Cloud computing resources 930 may analyze stored information and transmit commands or information to container 910 for display to the user.

In some embodiments, networked device 920 may be a cell phone, PDA, tablet, laptop, or other computing device. Networked device 920 may communicate directly with cloud computing resources 930 though communication link 950. Communication link 950 may be through WiFi, cellular link, or the like. Networked device 920 may use the link to receive a prescription plan stored in cloud computing resources 930. In some embodiments, networked device 920 may communicate the prescription plan to container 910 through communication link 960. Communication link 960 may be through Bluetooth®, Bluetooth® LE, ZigBee®, WiFi, or the like.

In some embodiments, networked device 920 may receive manual or automated input of user information (e.g., take a picture of a prescription or prescription bottle). Networked device 920 may also receive notifications from container 910 and/or process and send notifications to container 910.

FIG. 10 illustrates a suitable computing environment 1000 in which the described technologies can be implemented, including general-purpose or special-purpose computing environments. For example, the computing unit integrated into container 910 and/or networked device 920 may be implemented using computing environment 1000 comprising a processing unit 1010, memory 1020, and storage 1030 storing computer-executable instructions. The computing environment may have additional features. For example, the computing environment 1000 may include one or more input devices 1040, one or more communication connections 1050, and one or more output devices 1060. An interconnection mechanism (not shown) such as a bus, controller, or network interconnects the components of the computing environment 1000. Typically, operating system software (not shown) provides an operating environment for other software executing in the computing environment 1000, and coordinates activities of the components of the computing environment 1000.

The input device(s) 1040 may be a touch input device such as a keyboard, mouse, pen, trackball, touch screen, or game controller, a voice input device, a scanning device, a digital camera, or another device that provides input to the computing environment 1000. The output device(s) 1060 may be a display, printer, speaker, or another device that provides output from the computing environment 1100.

The communication connection(s) 1050 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

The disclosed technologies for networked device 920 can also be implemented with other computer system configurations, including hand held devices, multiprocessor systems, microprocessor-based or programmable consumer electronics, network PCs, minicomputers, mainframe computers, a collection of client/server systems, and the like.

The disclosed technologies can also be practiced in distributed computing environments, such as cloud computing resources 930, where tasks are performed by remote processing devices that are linked through a communications network. In a distributed computing environment, program modules may be located in both local and remote memory storage devices.

The processing unit 1010 included, for example, in the computing environment 1000 may execute computer-executable instructions and may be a real or a virtual processor device. In a multi-processing system, multiple processing units execute computer-executable instructions to increase processing power. The memory 1020 can be volatile memory (e.g., registers, cache, RAM), non-volatile memory (e.g., ROM, EEPROM, flash memory, etc.), or some combination of the two. The memory 1020 can store software implementing any of the technologies described herein. For example, the memory 1020 can store an operating system and/or software implementing the functions of the connected container. Typically, operating system software provides an operating environment for other software executing in the computing environment, and coordinates activities of the components of the computing environment.

The computing environment 1000 may have additional features. For example, the computing environment 1000 can include computer-readable storage devices (e.g., storage 1030). Computer-readable storage devices may be removable or non-removable, and include magnetic disks, magnetic tapes or cassettes, CD-ROMs, CD-RWs, DVDs, or any other tangible, computer-readable media, which can be used to store information and which can be accessed within the system. The computer-readable storage devices can store software containing instructions for any of the technologies described herein.

Disclosed embodiments may implement computer-executable instructions, such as those included in program modules and executed in a computing environment on a target real or virtual processor device. Program modules may include routines, programs, libraries, objects, classes, components, data structures, etc., that perform particular tasks or implement particular abstract data types. The functionality of the program modules may be combined or split between program modules as desired in various embodiments. Computer-executable instructions for program modules may be executed a processing unit, as described above.

Various operations or functions of the example embodiments described above can be implemented as software code or instructions. Such content can be directly executable ("object" or "executable" form), source code, or difference code ("delta" or "patch" code). Software implementations of the embodiments described herein can be provided via an article of manufacture with the code or instructions stored thereon, or via a method of operating a communication interface to send data via the communication interface. A machine or computer-readable storage device can cause a machine to perform the functions or operations described, and includes any mechanism that stores information in a tangible form accessible by a machine (e.g., computing device, electronic system, and the like), such as recordable/non-recordable media (e.g., read only memory (ROM), random access memory (RAM), magnetic disk storage media, optical storage media, flash memory devices, and the like). Computer-readable storage devices store computer-readable instruction in a non-transitory manner and do not include signals per se.

The technologies described herein have many advantages in the field of medication adherence systems. For example, integrating a display screen into the floor of a medication dispenser may aid a user to more easily determine which pills are to be taken at prescribed times. The user need only have the container with pills and not another device in order to comply with a prescription regimen. Another advantage is that a prescribing physician may change a user's prescription at any time, and send the new information to the container to change what pills are taken at certain times. Because the pills are not pre-packaged, or mixed, they may be removed from the container in any combination without the user having to determine which pills from a mixture are correct.

Aspects of the embodiments and any of the methods described herein can be performed by computer-executable instructions stored in one or more computer-readable media (storage or other tangible media) or stored in one or more compute readable storage devices, as described herein. The computer-executable instructions can be organized into one or more computer-executable components or modules. Aspects of the embodiments can be implemented with any number and organization of such components or modules. For example, aspects of the disclosed embodiments are not limited to the specific computer-executable instructions or the specific components or modules illustrated in the figures and described herein. Other embodiments may include different computer-executable instructions or components having more or less functionality than illustrated and described herein.

The order of execution or performance of the operations in the disclosed embodiments illustrated and described herein is not essential, unless otherwise specified. That is, the operations can be performed in any order, unless otherwise specified, and embodiments can include additional or fewer operations than those disclosed herein. For example, it is contemplated that executing or performing a particular operation before, contemporaneously with, or after another operation is within the scope of aspects of the disclosed embodiments.

Having described the disclosed embodiments in detail, it will be apparent that modifications and variations are possible without departing from the scope of aspects as defined in the appended claims. For instance, elements of the illustrated embodiments may be implemented in software and/or hardware. In addition, the technologies from any embodiment or example can be combined with the technologies described in any one or more of the other embodiments or examples. In view of the many possible embodiments to which the principles of the disclosed technology may be applied, it should be recognized that the illustrated embodiments are examples of the disclosed technology and should not be taken as a limitation on the scope of the disclosed technology. Therefore, it is intended that all matter contained in the above description and shown in the accompanying drawings shall be interpreted as illustrative and not in a limiting sense.

The invention claimed is:

1. A container for dispensing medication comprising:
   one or more storage compartments, wherein the one or more compartments are dimensioned to store medication;
   a lid that covers the one or more storage compartments of the container to prevent the medication from falling out of the container when the lid is closed, wherein the container and the lid are sized to fit within a pants pocket or a purse;
   a computing unit configured to process information about contents of the one or more storage compartments; and one or more display screens disposed on an interior surface of the container and coupled to the computing unit, the one or more display screens configured to display the information about the contents of one or more storage compartments.

2. The container of claim 1, wherein the one or more display screens are touch sensitive.

3. The container of claim 1, further comprising a communication module coupled to the computing unit and configured to communicate with a portable communications device.

4. The container of claim 1, wherein the computing device is configured to track medication regiments.

5. The container of claim 1, wherein the one or more display screens are configured to indicate that a storage compartment contains too little medication.

6. The container of claim 1, wherein the one or more display screens are configured to indicate that a storage compartment contains too much medication.

7. The container of claim 1, wherein the computing unit is further configured to receive prescription details about the medication in the one or more storage compartments.

8. The container of claim 1, wherein the one or more display screens are further configured to display the information independently in each of the one or more storage compartments.

9. The container of claim 8, wherein the information indicates an action to be taken with respect to the medication in the respective one or more storage compartments.

10. The container of claim 9, wherein the information is a predetermined color based on the action to be taken.

11. The container of claim 1, further comprising a sensor configured to detect a quantity of medication stored in the one or more storage compartments.

12. The container of claim 11, wherein the sensor comprises at least one of a force transducer, a capacitive touch sensor, or a camera.

13. The container of claim 12, wherein the force transducer is integrated into the one or more displays.

14. The container of claim 12, wherein the camera is integrated into a lid of the container and the camera is configured to take images of the contents of the one or more storage compartments.

15. The container of claim 1, further comprising a communication module coupled to the computing unit and configured to communicate with cloud computing resources.

16. The container of claim 15, wherein the communication module communicates using cellular telephone protocols.

17. The container of claim 1, further comprising a second display screen disposed on the lid of the container.

18. The container of claim 17, wherein the second display screen is visible when the container is closed.

19. The container of claim 17, wherein the second display screen is configured to display summary information about the contents of the container and/or battery life.

20. The container of claim 17, wherein the second display screen is touch sensitive.

21. A method of tracking medication usage, the method comprising:
displaying, by a first display screen disposed on an interior surface of a storage compartment of a container, an indication to add medication to the storage compartment, wherein the first display screen is visible when the container is open;
determining an amount of medication in the storage compartment;
comparing the amount of medication in the storage compartment with a predetermined amount of medication;
displaying a first message on the first display screen, the first message based on the comparison of the amount of medication in the storage compartment with the predetermined amount of medication; and
displaying a second message on a second display screen disposed on a lid of the container, the second display screen visible when the container is closed.

22. The method of claim 21, wherein the second message is a summary of contents of the container or a prompt to take medication.

23. The method of claim 21, wherein the storage compartment comprises a plurality of sub-compartments, and the first display screen is configured to display separate indications for each sub-compartment.

24. The method of claim 21, wherein determining the amount of medication in the storage compartment comprises using a sensor configured to determine the amount of medication in the storage compartment.

25. The method of claim 24, wherein the sensor is one of a force sensor integrated into the first display screen, a camera, or a capacitive touch sensor.

26. A method of tracking medication usage, the method comprising:
receiving a prescription plan by a computing unit of a medication container;
displaying, with a first display screen disposed on an inside of the container, a first message including an amount of medication required in the container pursuant to the prescription plan, wherein the first display screen is viewable by a user when the container is open; and
displaying, with a second display screen disposed on an exterior surface of the container, a second message, wherein the second display screen is viewable by the user when the container is closed.

27. A container for dispensing medication comprising:
one or more storage compartments, wherein the one or more compartments are dimensioned to store medication;
a computing unit configured to process information about contents of the one or more storage compartments;
one or more display screens disposed on an interior surface of the container and coupled to the computing unit, the one or more display screens configured to display the processed information about the contents of one or more storage compartments; and
a second display disposed on a lid of the container.

* * * * *